US010744006B2

(12) United States Patent
Vipparla

(10) Patent No.: US 10,744,006 B2
(45) Date of Patent: Aug. 18, 2020

(54) PET PROSTHETIC

(71) Applicant: Sai Vipparla, Milford, CT (US)

(72) Inventor: Sai Vipparla, Milford, CT (US)

( * ) Notice: Subject to any disclaimer, the term of this patent is extended or adjusted under 35 U.S.C. 154(b) by 44 days.

(21) Appl. No.: 16/247,970

(22) Filed: Jan. 15, 2019

(65) Prior Publication Data

US 2020/0222210 A1 Jul. 16, 2020

(51) Int. Cl.
*A61F 2/58* (2006.01)
*A61F 2/60* (2006.01)
*A61F 2/64* (2006.01)
*A61D 9/00* (2006.01)

(52) U.S. Cl.
CPC ............... *A61F 2/60* (2013.01); *A61D 9/00* (2013.01); *A61F 2002/607* (2013.01)

(58) Field of Classification Search
CPC ...... A61F 2/58; A61F 2/60; A61F 2/64; A61F 2/642; A61F 2/644; A61F 2002/307; A61F 2250/0081
USPC ...................................................... 623/40–42
See application file for complete search history.

(56) References Cited

U.S. PATENT DOCUMENTS

| 3,553,738 | A | * | 1/1971 | Liberson | A61F 2/604 |
| | | | | | 623/24 |
| 6,908,489 | B2 | * | 6/2005 | Didrick | A61F 2/586 |
| | | | | | 623/64 |
| D632,790 | S | * | 2/2011 | Cheng | D24/155 |
| 9,089,402 | B2 | * | 7/2015 | Campbell | A61F 5/0123 |
| 9,707,102 | B2 | * | 7/2017 | Thompson, Jr. | A61F 2/76 |
| 2013/0268092 | A1 | * | 10/2013 | Karlsson | A61F 2/80 |
| | | | | | 623/43 |
| 2017/0100264 | A1 | * | 4/2017 | Goldfarb | A61F 2/60 |

* cited by examiner

*Primary Examiner* — Bruce E Snow
(74) *Attorney, Agent, or Firm* — Cantor Colburn LLP

(57) ABSTRACT

A pet prosthetic for a stump of an animal including: a clamp portion configured to clamp to an upper portion of the stump above an elbow joint of the animal or a knee joint of the animal; a stump holder configured to receive the lower portion of the stump below the elbow joint of the animal or the knee joint of the animal; a stump holder cradle configured to receive and support the stump holder; a left rear support operably connecting the clamp portion to the stump holder cradle; a right rear support operably connecting the clamp portion to the stump holder cradle; an ankle joint operably connected to the stump holder cradle; a left forward support operably connecting the clamp portion to the ankle joint; a right forward support operably connecting the clamp portion to the ankle joint; and an artificial paw operably connected to the ankle joint.

17 Claims, 5 Drawing Sheets

PET PROSTHETIC

BACKGROUND

The subject matter disclosed herein relates to a pet prosthetic.

Animals may be born without portions of limbs or may lose limbs throughout their life due to various reasons including but not limited to injury or disease. The loss of the limb may create partial limb or a stump leading to difficulties walking for the animal

BRIEF DESCRIPTION

According to an embodiment, a pet prosthetic for a stump of an animal is provided. The pet prosthetic including: a clamp portion configured to clamp to an upper portion of the stump above an elbow joint of the animal or a knee joint of the animal; a stump holder configured to receive the lower portion of the stump below the elbow joint of the animal or the knee joint of the animal; a stump holder cradle configured to receive and support the stump holder; a left rear support operably connecting the clamp portion to the stump holder cradle; a right rear support operably connecting the clamp portion to the stump holder cradle; an ankle joint operably connected to the stump holder cradle; a left forward support operably connecting the clamp portion to the ankle joint; a right forward support operably connecting the clamp portion to the ankle joint; and an artificial paw operably connected to the ankle joint.

In addition to one or more of the features described above, or as an alternative, further embodiments may include that the ankle joint further includes: a housing: and an S link at least partially enclosed within the housing.

In addition to one or more of the features described above, or as an alternative, further embodiments may include that the clamp portion further includes: a forward clamp: and a rear clamp opposite the forward clamp.

In addition to one or more of the features described above, or as an alternative, further embodiments may include that the left forward support further includes: an upper end including an upper through hole; and a lower end opposite the upper end, wherein the forward clamp includes a left forward through hole, and wherein the left forward support is operably connected to the forward clamp by a fastening mechanism located within the upper through hole of the upper end and the left forward through hole.

In addition to one or more of the features described above, or as an alternative, further embodiments may include that the right forward support further includes: an upper end including an upper through hole; and a lower end opposite the upper end, wherein the forward clamp includes a right forward through hole, and wherein the right forward support is operably connected to the forward clamp by a fastening mechanism located within the upper through hole of the upper end and the right forward through hole.

In addition to one or more of the features described above, or as an alternative, further embodiments may include that the left rear support further includes: an upper end including an upper through hole; and a lower end opposite the upper end, wherein the rear clamp includes a left rear through hole, and wherein the left rear support is operably connected to the rear clamp by a fastening mechanism located within the upper through hole of the upper end and the left rear through hole.

In addition to one or more of the features described above, or as an alternative, further embodiments may include that the right rear support further includes: an upper end including an upper through hole; and a lower end opposite the upper end, wherein the rear clamp includes a right rear through hole, and wherein the right rear support is operably connected to the rear clamp by a fastening mechanism located within the upper through hole of the upper end and the right rear through hole.

In addition to one or more of the features described above, or as an alternative, further embodiments may include that the housing further includes: a left side; a right side opposite the left side; and an upper forward shield located on a forward end of the housing proximate an upper end of the housing, the upper forward shield extending from the left side to the right side.

In addition to one or more of the features described above, or as an alternative, further embodiments may include that the housing further includes: a forward upper through hole extending from the left side to the right side through the upper forward shield, wherein the lower end of the left forward support further includes a lower through hole, wherein the lower end of the right forward support further includes a lower through hole, and wherein the left forward support and the right forward support are operably connected to the housing through a pin located within the forward upper through hole, the lower through hole of the left forward support, and the lower through hole of the right forward support 148.

In addition to one or more of the features described above, or as an alternative, further embodiments may include that the stump holder cradle further includes: a left side; a right side opposite the left side; and a stub slot extending from a left side of the stub holder cradle to the right side of the stub holder cradle.

In addition to one or more of the features described above, or as an alternative, further embodiments may include that the lower end of the left rear support further includes: a stub portion, wherein the left rear support is operably connected to the stump holder cradle by the stub portion located within the stub slot.

In addition to one or more of the features described above, or as an alternative, further embodiments may include that the lower end of the right rear support further includes: a stub portion, wherein the right rear support is operably connected to the stump holder cradle by the stub portion located within the stub slot.

In addition to one or more of the features described above, or as an alternative, further embodiments may include that the housing further includes: a lower forward shield located on the forward end of the housing proximate a lower end of the housing, the forward shield extending from the left side to the right side, wherein the left side, the right side, the upper forward shield, and the lower forward shield partially enclose a cavity formed therebetween, the S link being located at least partially in the cavity.

In addition to one or more of the features described above, or as an alternative, further embodiments may include that the stump holder further includes: a left support guide including a through hole configured to fit the left rear support, the left rear support extending through the through hole of the left support guide; and a right support guide including a through hole configured to fit the right rear support, the right rear support extending through the through hole of the right support guide.

In addition to one or more of the features described above, or as an alternative, further embodiments may include that the forward clamp further includes a left strap slot and a right strap slot, the rear clamp includes a left strap slot and a right strap slot.

In addition to one or more of the features described above, or as an alternative, further embodiments may include: a flexible strap located within the left strap slot, the right strap slot, the left strap slot, and the right strap slot.

According to another embodiment, a method of assembling a pet prosthetic for a stump of an animal is provided. The method including: inserting an S link at least partially into a housing; operably connecting an artificial paw to the S link and the housing; operably connecting a stump holder cradle to the housing, the stump holder cradle including a cradle portion; inserting a stump holder into the stump holder cradle portion, the stump holder configured to receive a lower portion of the stump below an elbow joint of the animal or a knee joint of the animal; operably connecting a left rear support to the stump holder cradle and a clamp portion, the clamp portion configured to clamp to an upper portion of the stump above the elbow joint of the animal or the knee joint of the animal; operably connecting a right rear support to the stump holder cradle and the clamp portion; operably connecting a left forward support to the housing and the clamp portion; and operably connecting a right forward support to the housing and the clamp portion.

BRIEF DESCRIPTION OF THE DRAWINGS

The following descriptions should not be considered limiting in any way. With reference to the accompanying drawings, like elements are numbered alike.

DETAILED DESCRIPTION

A detailed description of an embodiment of the disclosed apparatus and method are presented herein by way of exemplification and not limitation with reference to the Figures.

Figure 1:
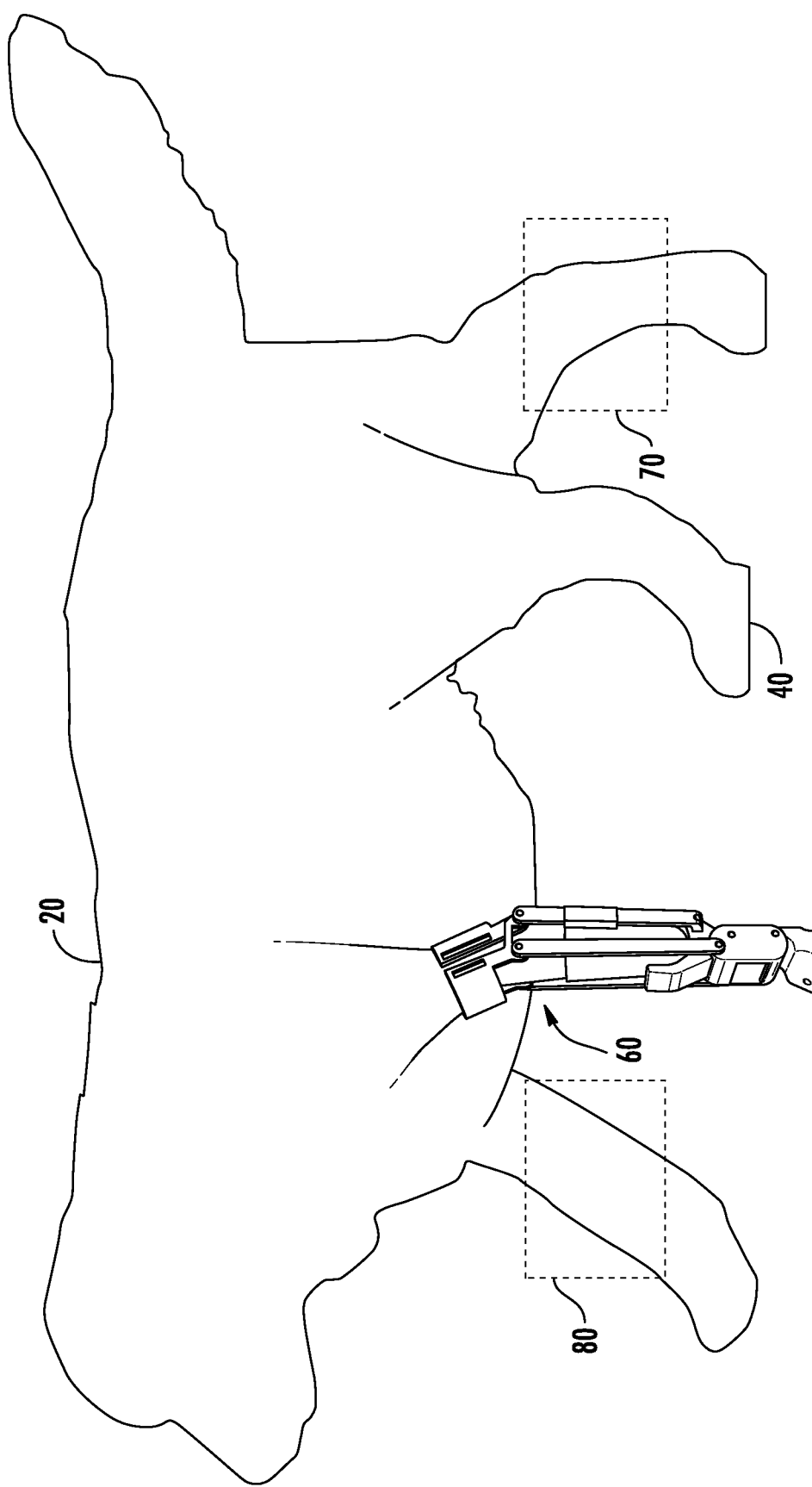
FIG. 1 illustrates an embodiment of a pet prosthetic installed on an animal, according to an embodiment of the present disclosure.

FIG. 1 schematically illustrates an embodiment of a pet prosthetic 100. Animals 20 may be born without portions of limbs or may lose portions of limbs throughout their life due to various reasons including but not limited to injury or disease. The loss of a portion of a limb may create partial limb or a stump 60. The pet prosthetic 100 is configured to receive the stump 60 of the animal 20 and securely attached to the stump 60. The pet prosthetic 100 may be configured to secure around the elbow joint 80 or knee joint 70 of the animal 20. It is understood that while the animal is shown as a dog in FIG. 1, the pet prosthetic 100 may be utilized for any animal.

Figure 2:
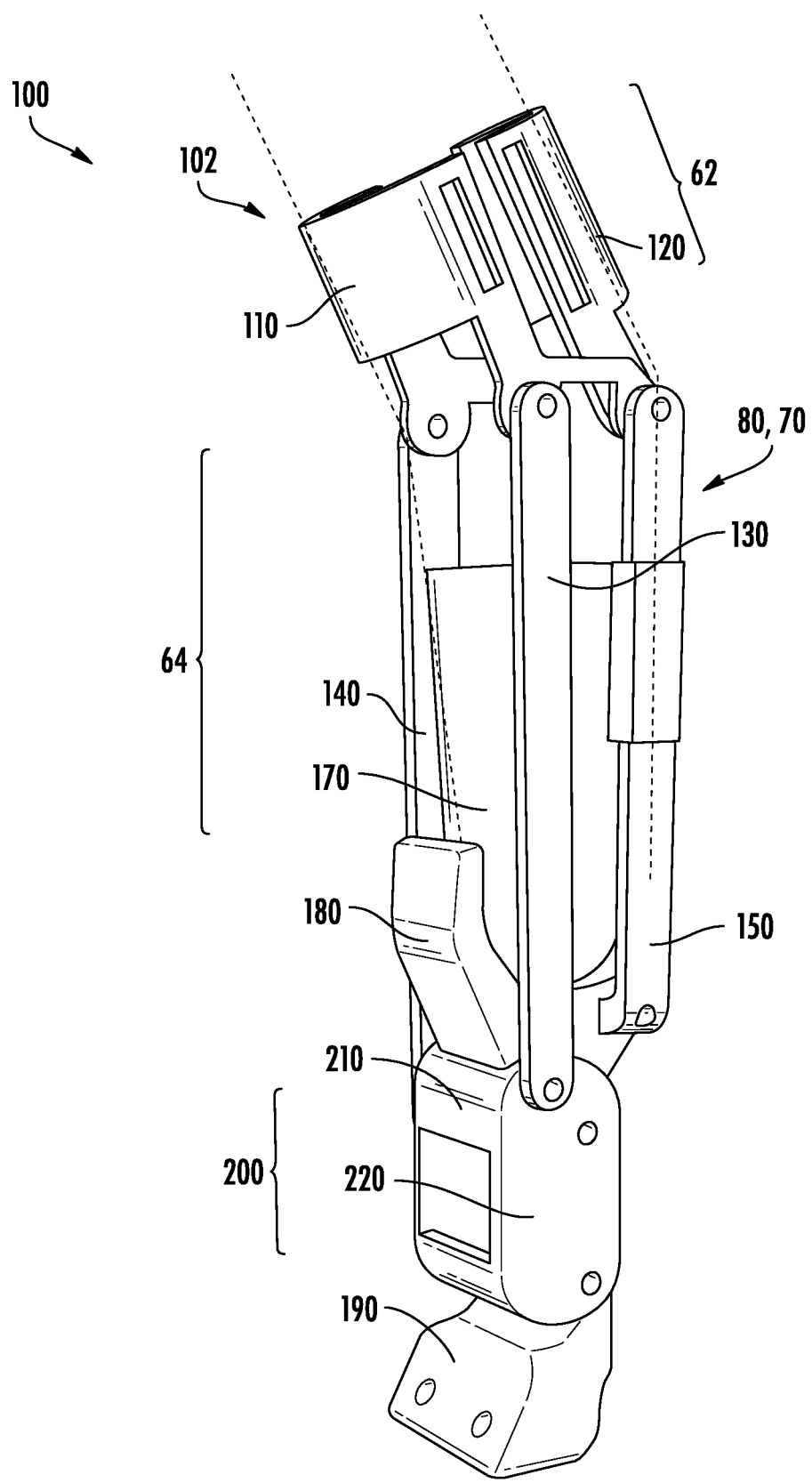
FIG. 2 illustrates an enlarged view of the pet prosthetic of FIG. 1, according to an embodiment of the present disclosure.

Referring now to FIG. 2, with continued reference to FIG. 1, an enlarged view of the pet prosthetic 100 is illustrated. The pet prosthetic 100 comprises a clamp portion 102 configured to clamp to an upper portion 62 of the stump 60 above the elbow joint 80 or knee joint 70 of the animal 20. The clamp portion 102 may be composed of a forward clamp 110 and a rear clamp 120 opposite the forward clamp 110. The forward clamp 110 and the rear clamp 120 together provide about 360 degrees of support around the upper portion 62 of the stump 60. The forward clamp 110 and the rear clamp 120 together may be operably shaped to provide a secure and comfortable fit to the upper portion 62 of the stump 60. The pet prosthetic 100 comprises a stump holder 170 configured to receive the lower portion 64 of the stump 60. The stump holder 170 may be operably shaped to cradle the stump 60 to provide both a comfortable and secure fit for the stump 60 of the animal 20. The pet prosthetic 100 further comprises a stump holder cradle 180 configured to receive and support the stump holder 170. The stump holder 170 is configured to fit in the stump holder cradle 180, as show in FIG. 2. The clamp portion 102 is operably connected to the stump holder cradle 180 and an ankle joint 200 through four separate supports including a left forward support 130, a right forward support 140, a left rear support 150, and a right rear support 160 (see FIG. 3). The ankle joint 200 that allows the pet prosthetic 100 to bend around the same area where a natural ankle joint would be located in a healthy limb of an animal 20. The ankle joint 200 is composed of a housing 220 and an S link 210 enclosed with the housing 220. Lastly, the pet prosthetic 100 further comprises an artificial paw 190 operably connected to the ankle joint 200. The artificial paw 190 may be rotatable relative to the ankle joint 200.

Figure 3:
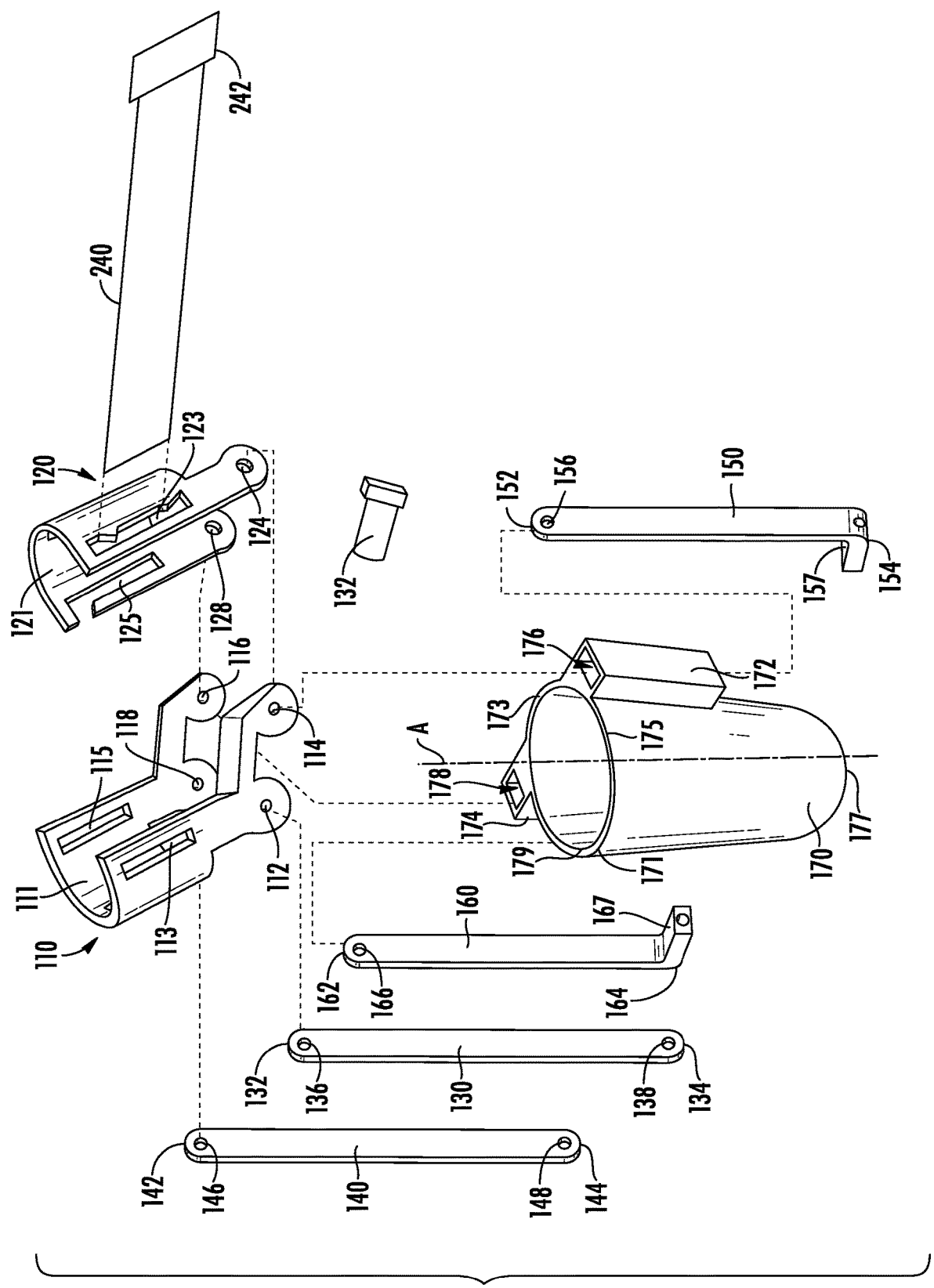
FIG. 3 illustrates an enlarged exploded view of the pet prosthetic of FIG. 1, according to an embodiment of the present disclosure.
Figure 4:
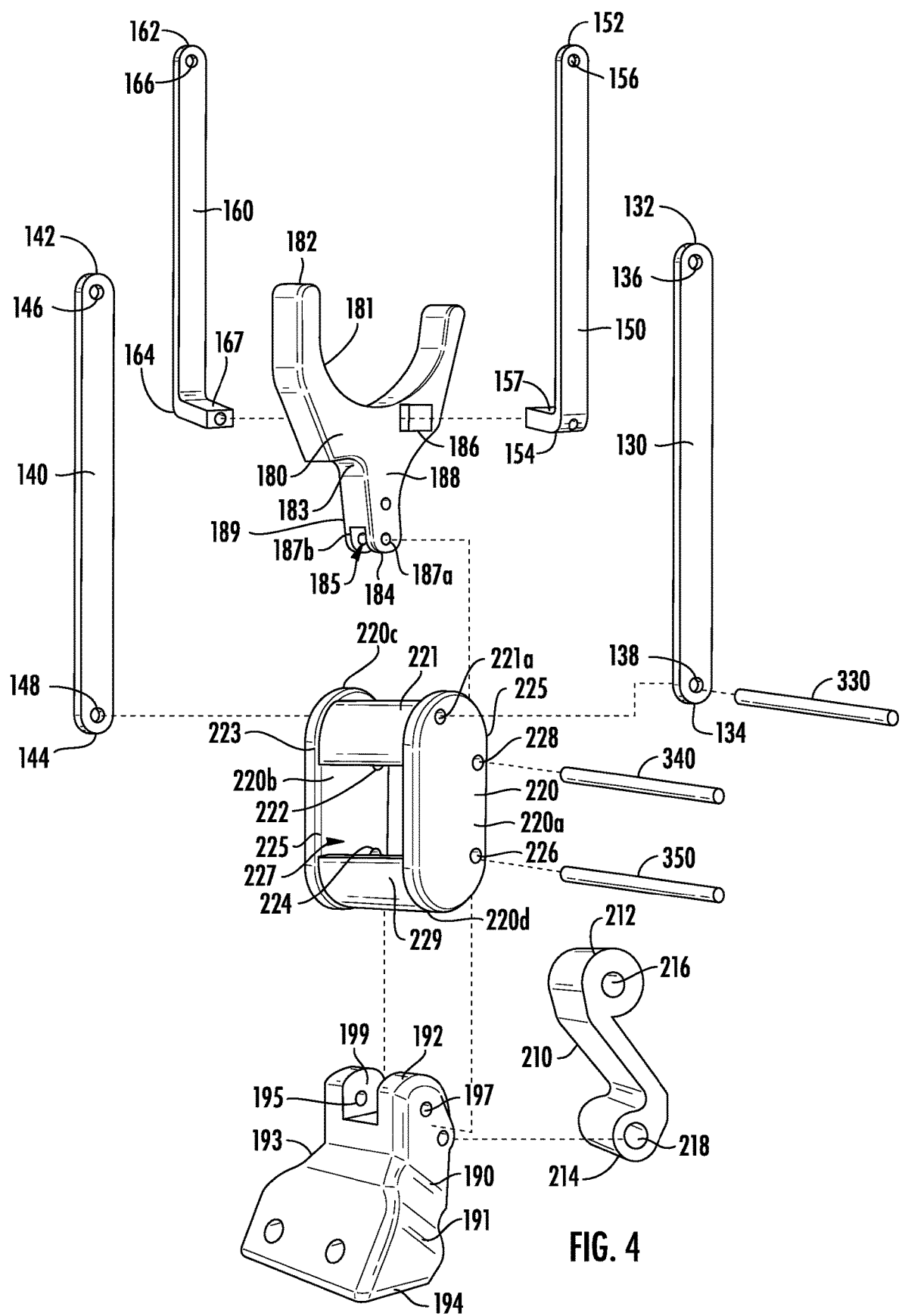
FIG. 4 illustrates an enlarged exploded view of the pet prosthetic of FIG. 1, according to an embodiment of the present disclosure.

Referring now to FIGS. 3 and 4, with continue reference to FIGS. 1-2, an enlarged exploded view of the pet prosthetic is illustrated. As mentioned above, the clamp portion 102 includes a forward clamp 110 and a rear clamp 120. The forward clamp 110 includes a concave portion 111 configured to receive the upper portion 62 of the stump 60. The forward clamp 110 also includes a left forward through hole 112, a right forward through hole 118, a left rear through hole 114, and a right rear through hole 116. The forward clamp 110 further includes a left strap slot 113 and a right strap slot 115. The rear clamp 120 includes a concave portion 121 configured to receive the upper portion 62 of the stump 60. The rear clamp 120 also includes a left through hole 124 and a right through hole 128. The rear clamp 120 further includes a left strap slot 123 and a right strap slot 123. A flexible strap 240 may be inserted through (i.e., located within) the left strap slot 113, the right strap slot 115, the left strap slot 123, and the right strap slot 125 and then secured in place (e.g., tightened, snapped, buttoned, etc.). The flexible strap 240 may be composed of a flexible material, such as, for example, a fabric, rubber, rope, etc. The flexible strap 240 may include a fastening mechanism 242 to secure the flexible strap 240 in place once the flexible strap 240 is tightened in the left strap slot 113, the right strap slot 115, the left strap slot 123, and the right strap slot 125. The fastening mechanism 242 may be a fastening feature, such as, for example, a buckle, a button, a snap, a hook and loop, etc. The forward clamp 110 and the rear clamp 120 may each be fabricated through additive manufacturing and configured to mirror or match the shape of the upper portion 62 of the stump 60 to ensure a secure, comfortable, and perfect fit for the animal 20.

As mentioned above, the clamp portion 102 is operably connected to the stump holder 170 through the left forward support 130, the right forward support 140, the left rear support 150, and the right rear support 160. As shown in FIG. 3, the left forward support 130 includes an upper end 132 and a lower end 134 opposite the upper end 132. The upper end 132 includes an upper through hole 136 and the lower end 134 includes a lower through hole 138. The upper through hole 136 of the upper end 132 is configured to align with the left forward through hole 112 of the forward clamp 110. A fastening mechanism 132 may be inserted through (i.e., located within) the upper through hole 136 and the left forward through hole 112 to operably connect the forward clamp 110 and the left forward support 130. The fastening mechanism 132 may be a bolt and nut, screw, rivet, etc.

The right forward support 140 includes an upper end 142 and a lower end 144 opposite the upper end 142. The upper end 142 includes an upper through hole 146 and the lower end 144 includes a lower through hole 148. The upper through hole 146 of the upper end 142 is configured to align with the right forward through hole 118 of the forward clamp 110. A fastening mechanism 132 may be inserted through the upper through hole 146 and the right forward through hole 118 to operably connect the forward clamp 110 and the right forward support 140.

The left rear support 150 includes an upper end 152 and a lower end 154 opposite the upper end 152. The upper end 152 includes an upper through hole 156 and the lower end 154 includes a stub portion 157. The upper through hole 156 of the upper end 152 is configured to align with the left rear through hole 114 of the forward clamp 110 and the left through hole 124 of the rear clamp 120. A fastening mechanism 132 may be inserted through the upper through hole 156, the left rear through hole 114, and the left through hole 124 to operably connect the forward clamp 110, the rear clamp 120, and the left rear support 150.

The right rear support 160 includes an upper end 162 and a lower end 164 opposite the upper end 162. The upper end 162 includes an upper through hole 166 and the lower end 164 includes a stub portion 167. The upper through hole 166 of the upper end 162 is configured to align with the right rear through hole 116 of the forward clamp 110 and the right through hole 128 of the rear clamp 120. A fastening mechanism 132 may be inserted through the upper through hole 166, the right rear through hole 116, and the right through hole 128 to operably connect the forward clamp 110, the rear clamp 120, and the right rear support 160.

As shown in FIG. 3, the stump holder 170 may include a left support guide 172 and a right support guide 174 opposite the left rear support guide 172. The left support guide 172 and the right support guide 178 may be located proximate a rear end 173 of the stump holder 170. The rear end 173 is opposite a forward end 171, as shown in FIG. 3 The left support guide 172 includes a through hole 176 configured to fit the left rear support 150. The right support guide 174 includes a through hole 178 configured to fit the right rear support 160.

The upper end 152 of left rear support 150 may be inserted into the through hole 176 of the left support guide 172 with the stub portion 157 facing inward towards a center A of the pet prosthetic 100. The upper end 162 of right rear support 160 may be inserted into the through hole 178 of the right support guide 174 with the stub portion 167 facing inward towards a center A of the pet prosthetic 100.

The stump holder 170 is configured to receive the lower portion 64 of the stump 60 through an opening 175 in a top 179 of the stump holder. The opening 175 may be circular or oval in shape. The stump holder 170 may be operably shaped to cradle the stump 60 to provide both a comfortable and secure fit for the stump 60 of the animal 20. The stump holder 170 may be fabricated through additive manufacturing and configured to mirror or match the shape of the lower portion 64 of the stump 60 to ensure a secure, comfortable, and perfect fit for the animal 20. The bottom 177 of the stump holder 170 may have a dome shape, as shown in FIG. 3. It is understood that the embodiments disclosed herein are not limited to the bottom 177 being a dome shape as illustrated in FIG. 3, thus the bottom 177 of the stump holder 170 may also have a spherical radius shape, a parabolic shape, a cone shape, a blunt shape, a stepped shape, or any other geometric shape known to one of skill in the art.

The stump holder 170 is configured to fit in a stump holder cradle 180, as show in FIGS. 2 and 4. The stump holder cradle 180 includes an upper end 182 and a lower end 184 opposite of the upper end 182. The stump holder cradle 180 includes cradle portion 181 at the upper end 182. The cradle portion 181 initiates at the upper end 182 and extends into the stump holder cradle 180. The cradle portion 181 is operably shaped to match the shape of the stump holder 170. In an embodiment, the cradle portion 181 may have a "U" shape, as show in FIG. 4. The stump holder cradle 180 may include a stub slot 186 extending from a left side 188 of the stump holder cradle 180 to a right side 189 of the stump holder cradle 180. The stub slot 186 is configured to receive the stub portion 157 of the left rear support 150 on the left side 188 of the stump holder cradle 180. The stub slot 186 is configured to receive the stub portion 167 of the right rear support 160 on the right side 189 of the stump holder cradle 180. The stump holder cradle 180 also includes a gap 185 that separates the left side 188 from the right side 189. The gap is located proximate the lower end 184 of the stump holder cradle 180. A lower left through hole 187a extends from the left side 188 to the gap 185 and a lower right through hole 187b be extends from the right side 189 to the gap 185. The lower left through hole 187a is aligned with the lower right through hole 187b. The gap 185 is configured to receive an upper end 212 of the S link.

The housing 220 includes a left side 220a and a right side 220b. The housing 220 also includes an upper forward shield 221 proximate an upper end 220c and a lower forward shield 229 proximate a lower end 220d. The upper forward shield 221 extends from the left side 220a to the right side 220b. A shelf 183 of the stump holder cradle 180 rests upon the upper forward shield 221. The upper forward shield 221 is located on a forward end 223 of the housing 220. The housing 220 also includes a rear end 225 opposite the forward end 223. The housing 220 includes a forward upper through hole 221a that extends from the left side 220a to the right side 220b through the upper forward shield 221. The forward upper through hole 221a is configured to align with the lower through hole 138 of the left forward support 138, and the lower through hole 148 of the right forward support 148.

A pin 330 may be located within the forward upper through hole 221a, the lower through hole 138 of the left forward support 138, and the lower through hole 148 of the right forward support 140. The pin 330 allows the housing 220, the right forward support 140, and the left forward support 130 to rotated relative to each other. The pin 330 may be secured within the forward upper through hole 221a, the lower through hole 138 of the left forward support 138, and the lower through hole 148 of the right forward support 140 by one or more nuts and/or one or more swaged ends.

The housing 220 includes an upper right rear through hole 222 on the right side 220b and an upper left rear through hole 228 on the left side 220b. The upper left rear through hole 228 is aligned with the upper right rear through hole 222. The housing 220 also includes a lower right rear through hole 224 on the right side 220b and a lower left through hole 226 on the left side 220b. The lower right rear through hole 224 is aligned with the lower left through hole 226. The left side 220a, the right side 220b, the upper forward shield 221, and the lower forward shield 229 partially enclose a cavity 227 formed therebetween. The S link 210 is located at least partially in the cavity 227.

The S link 210 is configured to fit at least partially within the cavity 227. As shown in FIG. 4, the S link 210 has an "S" shape as shown in FIG. 4. Advantageously, the "S" shape provides impact absorption and flexibility for the pet prosthetic 100. The S link 210 includes an upper end 212 and a lower end 214 opposite the upper end 212. The S link 210 also includes an upper through hole 216 located proximate the upper end 212 and a lower through hole 218 located proximate the lower end 214. The upper through hole 216 is configured to align with the upper left rear through hole 228, the upper right rear through hole 222, the lower left through hole 187a, and the lower right through hole 187b when the S link 210 is located within the cavity 227 and the upper end 212 of the S link 212 is located within the gap 185 of the stump holder cradle 180.

A pin 340 may be located within the upper through hole 216, the upper left rear through hole 228, the upper right rear through hole 222, the lower left through hole 187a, and the lower right through hole 187b when the S link 210 is located within the cavity 227 and the upper end 212 of the S link 212 is located within the gap 185 of the stump holder cradle 180. The pin 340 allows the S link 210, the housing 220, and the stump holder cradle 180 to rotate relative to each other. The pin 340 may be secured within the upper through hole 216, the upper left rear through hole 228, the upper right rear through hole 222, the lower left through hole 187a, and the lower right through hole 187b by one or more nuts and/or one or more swaged ends.

The artificial paw 190 includes an upper end 192 and a lower end 194 opposite the upper end 192. The artificial paw includes a left side 191 and a right side 193 opposite the left side 191. A gap 199 may be located proximate the upper end 192 of the artificial paw 190. The artificial paw 190 may also include an upper left through hole 197 and an upper right through hole 195. The upper left through hole 197 extending from the left side 191 to the gap 199. The upper right through hole 195 extending from the right side 193 to the gap 199. The lower through hole 218 is configured to align with the lower right rear through hole 224 and the lower left through hole 226 when the S link 210 is located within the cavity 227 and the lower end 214 of the S link 210 is located in the gap 199 of the artificial paw 190.

A pin 350 may be located within the lower through hole 218, the lower right rear through hole 224, the lower left through hole 226, the upper left through hole 197, and the upper right through hole 195, when the S link 210 is located within the cavity 227 and the lower end 214 of the S link 210 is located in the gap 199 of the artificial paw 190. The pin 550 allows the S link 210, the housing 220, and the artificial paw 190 to rotate relative to each other. The pin 350 may be secured within the lower through hole 218, the lower right rear through hole 224, the lower left through hole 226, the upper left through hole 197, and the upper right through hole 195 by one or more nuts and/or one or more swaged ends.

Figure 5:
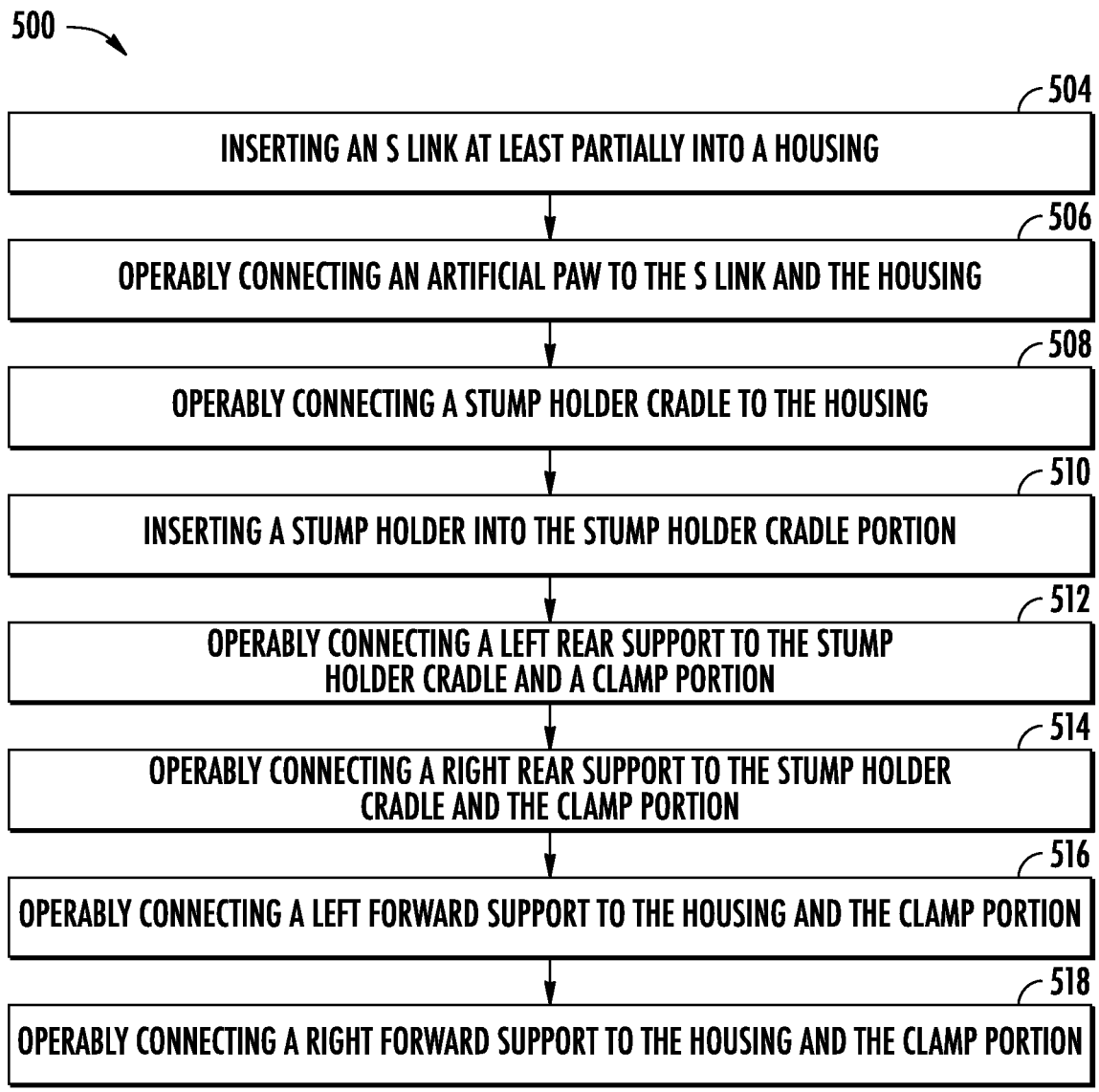
FIG. 5 is a flow chart of a method of assembling the pet prosthetic of FIGS. 1-4, according to an embodiment of the present disclosure.

Referring now to FIG. 5, with continued reference to FIGS. 1-4, a method 500 of assembling a pet prosthetic 100 for a stump 60 of an animal 20, in accordance with an embodiment of the present disclosure.

At block 504, an S link 210 is inserted at least partially into a housing 220. At block 506, an artificial paw 190 is operably connected to the S link and the housing 220. At block 508, a stump holder cradle 180 is operably connected to the housing 220. At block 810, a stump holder 170 is inserted into the stump holder cradle portion 181.

At block 812, a left rear support 150 is operably connected to the stump holder cradle 180 and a clamp portion 102. The upper end 152 of left rear support 150 may be inserted into the through hole 176 of the left support guide 172 prior to block 812. At block 814, a right rear support 160 is operably connected to the stump holder cradle 180 and the clamp portion 102. The upper end 162 of right rear support 160 may be inserted into the through hole 178 of the right support guide 174 prior to block 814.

At block 816, a left forward support 130 is operably connected to the housing 220 and the clamp portion 102. At block 818, a right forward support 140 is operably connected to the housing 220 and the clamp portion 102.

The method 500 may further comprise: producing, using additive manufacturing at least one of the S link 210, the housing 220, the artificial paw 190, the stump holder 170, the stump holder cradle 180, the left rear support 150, the right rear support 160, the left forward support 130, the right forward support 140, and the clamp portion 102. Additive manufacturing may include direct metal laser sintering, binder jet printing, three-dimensional printing, fused filament lamination, fused deposition modeling, selective laser sintering, direct metal laser sintering, electron beam melting, laminated object manufacturing, stereolithography, photopolymerization, or any additive manufacturing process known to one of skill in the art.

While the above description has described the flow process of FIG. 5 in a particular order, it should be appreciated that the ordering of the steps may be varied.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof Therefore, it is intended that the present disclosure not be limited to the particular embodiment disclosed as the best mode contemplated for carrying out this present disclosure, but that the present disclosure will include all embodiments falling within the scope of the claims.

What is claimed is:
1. A pet prosthetic for a stump of an animal, the pet prosthetic comprising:

a clamp portion configured to clamp to an upper portion of the stump above an elbow joint of the animal or a knee joint of the animal;
a stump holder configured to receive the lower portion of the stump below the elbow joint of the animal or the knee joint of the animal;
a stump holder cradle configured to receive and support the stump holder;
a left rear support operably connecting the clamp portion to the stump holder cradle;
a right rear support operably connecting the clamp portion to the stump holder cradle;
an ankle joint operably connected to the stump holder cradle;
a left forward support operably connecting the clamp portion to the ankle joint;
a right forward support operably connecting the clamp portion to the ankle joint; and
an artificial paw operably connected to the ankle joint.

2. The pet prosthetic of claim 1, wherein the ankle joint further comprises:
a housing: and
an S link at least partially enclosed within the housing.

3. The pet prosthetic of claim 2, wherein the housing further comprises:
a left side;
a right side opposite the left side; and
an upper forward shield located on a forward end of the housing proximate an upper end of the housing, the upper forward shield extending from the left side to the right side.

4. The pet prosthetic of claim 3, wherein the housing further comprises:
a forward upper through hole extending from the left side to the right side through the upper forward shield,
wherein the lower end of the left forward support further comprises a lower through hole,
wherein the lower end of the right forward support further comprises a lower through hole, and
wherein the left forward support and the right forward support are operably connected to the housing through a pin located within the forward upper through hole, the lower through hole of the left forward support, and the lower through hole of the right forward support.

5. The pet prosthetic of claim 3, wherein the housing further comprises:
a lower forward shield located on the forward end of the housing proximate a lower end of the housing, the forward shield extending from the left side to the right side,
wherein the left side, the right side, the upper forward shield, and the lower forward shield partially enclose a cavity formed therebetween, the S link being located at least partially in the cavity.

6. The pet prosthetic of claim 3, wherein the stump holder further comprises:
a left support guide including a through hole configured to fit the left rear support, the left rear support extending through the through hole of the left support guide; and
a right support guide including a through hole configured to fit the right rear support, the right rear support extending through the through hole of the right support guide.

7. The pet prosthetic of claim 1, wherein the clamp portion further comprises:
a forward clamp: and
a rear clamp opposite the forward clamp.

8. The pet prosthetic of claim 7, wherein the left forward support further comprises:
an upper end including an upper through hole; and
a lower end opposite the upper end,
wherein the forward clamp includes a left forward through hole, and
wherein the left forward support is operably connected to the forward clamp by a fastening mechanism located within the upper through hole of the upper end and the left forward through hole.

9. The pet prosthetic of claim 7, wherein the right forward support further comprises:
an upper end including an upper through hole; and
a lower end opposite the upper end,
wherein the forward clamp includes a right forward through hole, and
wherein the right forward support is operably connected to the forward clamp by a fastening mechanism located within the upper through hole of the upper end and the right forward through hole.

10. The pet prosthetic of claim 7, wherein the left rear support further comprises:
an upper end including an upper through hole; and
a lower end opposite the upper end,
wherein the rear clamp includes a left rear through hole, and
wherein the left rear support is operably connected to the rear clamp by a fastening mechanism located within the upper through hole of the upper end and the left rear through hole.

11. The pet prosthetic of claim 7, wherein the right rear support further comprises:
an upper end including an upper through hole; and
a lower end opposite the upper end,
wherein the rear clamp includes a right rear through hole, and
wherein the right rear support is operably connected to the rear clamp by a fastening mechanism located within the upper through hole of the upper end and the right rear through hole.

12. The pet prosthetic of claim 1, wherein the stump holder cradle further comprises:
a left side;
a right side opposite the left side; and
a stub slot extending from a left side of the stub holder cradle to the right side of the stub holder cradle.

13. The pet prosthetic of claim 12, wherein the lower end of the left rear support further comprises:
a stub portion,
wherein the left rear support is operably connected to the stump holder cradle by the stub portion located within the stub slot.

14. The pet prosthetic of claim 12, wherein the lower end of the right rear support further comprises:
a stub portion,
wherein the right rear support is operably connected to the stump holder cradle by the stub portion located within the stub slot.

15. The pet prosthetic of claim 1, wherein the forward clamp further includes a left strap slot and a right strap slot, the rear clamp includes a left strap slot and a right strap slot.

16. The pet prosthetic of claim 15, further comprising:
a flexible strap located within the left strap slot, the right strap slot, the left strap slot, and the right strap slot.

17. A method of assembling a pet prosthetic for a stump of an animal, the method comprising:
inserting an S link at least partially into a housing;

operably connecting an artificial paw to the S link and the housing;

operably connecting a stump holder cradle to the housing, the stump holder cradle including a cradle portion;

inserting a stump holder into the stump holder cradle portion, the stump holder configured to receive a lower portion of the stump below an elbow joint of the animal or a knee joint of the animal;

operably connecting a left rear support to the stump holder cradle and a clamp portion, the clamp portion configured to clamp to an upper portion of the stump above the elbow joint of the animal or the knee joint of the animal;

operably connecting a right rear support to the stump holder cradle and the clamp portion;

operably connecting a left forward support to the housing and the clamp portion; and operably connecting a right forward support to the housing and the clamp portion.

* * * * *